United States Patent [19]

Shimizu et al.

[11] Patent Number: 5,683,913
[45] Date of Patent: Nov. 4, 1997

[54] REGULATORY GENE FOR THE EXPRESSION OF NITRILE HYDRATASE GENE

[75] Inventors: Sakayu Shimizu, 14, Hakuraku-cho, Nishinokyo, Nakakyo-ku, Kyoto-shi, Kyoto 604; Michihiko Kobayashi, Kyoto, both of Japan

[73] Assignees: Sakayu Shimizu, Kyoto; Nitto Chemical Industry Co., Ltd., Tokyo, both of Japan

[21] Appl. No.: 537,434

[22] Filed: Oct. 2, 1995

[30] Foreign Application Priority Data

Oct. 3, 1994 [JP] Japan .................... 6-239263

[51] Int. Cl.$^6$ .................. C12N 1/00; C12N 5/10; C12N 15/31; C12N 15/63
[52] U.S. Cl. .................. 435/252.3; 435/254.11; 435/325; 435/320.1; 536/23.7
[58] Field of Search .................. 435/320.1, 325, 435/252.3, 254.11; 536/23.4

[56] References Cited

PUBLICATIONS

Kobayashi et al. "Cloning, nucleotide sequence and expression in *Escherichia coli* of two cobalt containing nitrile hydratase genes from Rhodococcus rhodochrous J1." Biochim. Biophys. Acta 1129:23–33, 1991.

*Primary Examiner*—Robert A. Wax
*Assistant Examiner*—Gabriele E. Bugaisky
*Attorney, Agent, or Firm*—Oblon, Spivak, McClelland, Maier & Neustadt, P.C.

[57] ABSTRACT

The invention relates to a regulatory gene coding for a polypeptide having the ability to activate a promoter for a nitrile hydratase gene, a recombinant DNA containing said regulatory gene, and a transformant transformed with said recombinant DNA.

The introduction of the regulatory gene of the invention along with a nitrile hydratase gene and its promoter region permits bacteria of the genus Rhodococcus to produce a higher level of nitrile hydratase. Other extraneous gene can also be introduced into a region downstream of the promoter to produce other proteins in high yield.

4 Claims, 2 Drawing Sheets

REGULATORY GENE FOR THE EXPRESSION OF NITRILE HYDRATASE GENE

FIELD OF THE INVENTION

The present invention relates to a regulatory gene derived from bacteria of the genus Rhodococcus and coding for a polypeptide capable of activating a promoter for a nitrile hydratase gene, a recombinant DNA containing said DNA, and a transformant transformed with said recombinant DNA.

BACKGROUND OF THE INVENTION

Processes for producing amides by nitrile hydratase that is an enzyme hydrating nitriles to amides came to be used as industrially advantageous methods by virtue of the reaction at normal temperature and pressure, higher conversion degree, etc. In particular, bacteria of the genus Rhodococcus are known to accumulate a significant amount of the enzyme in their cells to exhibit high catalytic activity (see Japanese Patent Publication No. 4873/1992 and Japanese Laid-Open Patent Publication Nos. 91189/1987, 470/1990 and 84198/1990).

As compared with such conventional processes, those using a nitrile hydratase gene cloned by genetic recombination are expected to attain drastic improvements in the catalytic ability of bacteria to hydrate nitriles because the bacteria can be engineered to contain multiple copies of the same gene. Further improvements in the enzyme are also facilitated by genetic recombination techniques such as site-specific mutagenesis, random mutagenesis, etc. A nitrile hydratase gene derived from the genus Rhodococcus has been obtained from N-774 (Japanese Laid-Open Patent Publication No. 119778/1990) and J-1 (Japanese Laid-Open Patent Publication No. 211379/1992). The nitrile hydratase gene from N-774 could successfully inserted into a Rhodococcus—E. coli hybrid plasmid vector (Japanese Laid-Open Patent Publication No. 64589/1993) and attained high activity when introduced into bacteria of the genus Rhodococcus (Japanese Laid-Open Patent Publication No. 68566/1993). On the other hand, there is no report on the expression of the nitrile hydratase gene derived from *Rhodococcus rhodochrous* J-1 in bacteria of the genus Rhodococcus, in spite of its higher nitrile hydratase activity than N-774.

SUMMARY OF THE INVENTION

The present inventors speculated that the failure to express the gene derived from J-1 results from the absence in the DNA fragment of a regulatory gene involved in function of a promoter for the nitrile hydratase gene. Hence, they sought for the regulatory gene in total DNA from J-1 and found the gene located upstream of the nitrile hydratase structural gene. This gene was successfully used for the high-level expression of nitrile hydratase in a transformant of the genus Rhodococcus.

That is, the present invention relates to a regulatory gene derived from bacteria of the genus Rhodococcus and coding for a polypeptide capable of activating a promoter for the nitrile hydratase gene, a recombinant DNA containing said DNA, and a transformant transformed with said recombinant DNA.

DETAILED DESCRIPTION OF THE INVENTION

Figure 1:
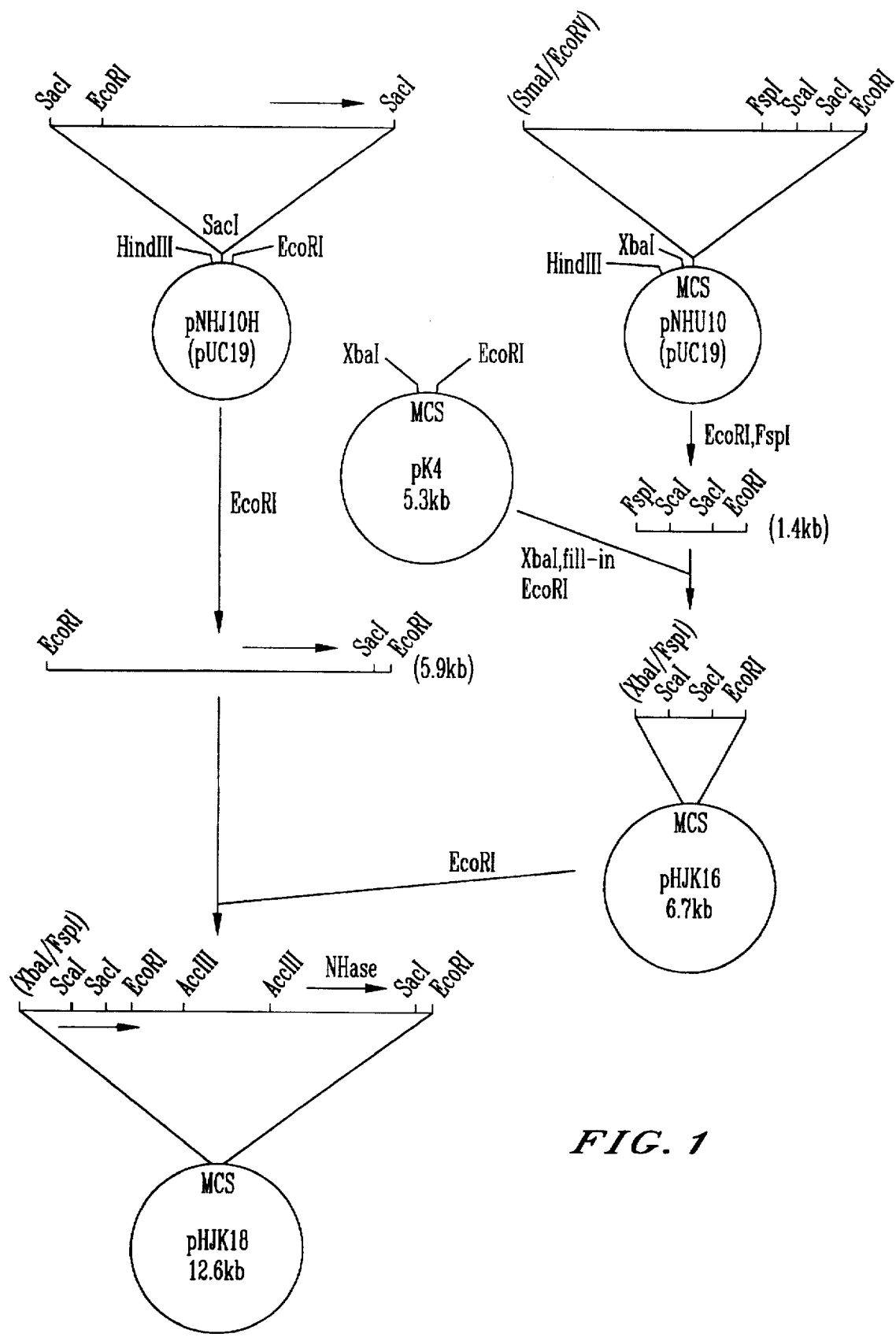
FIG. 1 shows the construction scheme of the recombinant plasmid pHJK18.

Hereinafter, the present invention is described in detail. The present invention is practiced in the following steps.

(1) Preparation of chromosomal DNA

Total DNA is isolated from *Rhodococcus rhodochrous* J-1.

(2) Construction of a DNA Library

The fragment of the target nitrile hydratase gene is excised from a plasmid containing the nitrile hydratase gene from J-1 and then labeled with a radioisotope. This fragment is used as a probe.

The total DNA obtained in step (1) is cleaved with restriction enzymes and subjected to Southern hybridization (Southern E. M., J. Mol. Biol. 98, 503 (1975)) with the probe prepared above. The detected DNA fragments containing the target gene are inserted into a plasmid vector pUC19 to prepare a library.

(3) Preparation of transformants and selection of a recombinant DNA

The recombinant DNA library constructed in step (2) is used for preparation of transformants from which a colony carrying the target recombinant DNA is selected by colony hybridization (R. Bruce Wallace et al., Nuc. Acids Res. 9, 879 (1981)) using the probe obtained in step (2). The hybridized colony is further subjected to Southern hybridization so that the presence of the target recombinant DNA is confirmed.

(4) Isolation and purification of a recombinant plasmid and construction of a restriction enzyme map A recombinant plasmid is isolated from the transformant obtained in step (3). This plasmid is designated plasmid pNHU10. It is cleaved with various restriction enzymes and analyzed by electrophoresis to prepare a restriction enzyme map.

(5) Construction of a recombinant plasmid by inserting a fragment containing a regulatory gene and the nitrile hydratase gene into a plasmid vector capable of replicating in the genus Rhodococcus Recombinant plasmids pHK18 and pHK19, each carrying a regulatory gene and a fragment containing a nitrile hydratase gene, are constructed by inserting the plasmid obtained in step (4) and plasmid pNHJ10H containing the nitrile hydratase gene derived from J-1 into the hybrid plasmid vector pK4.

(6) Transformation of bacteria of the genus Rhodococcus and production of nitrile hydratase by the transformant The plasmid obtained in step (5) is introduced into bacteria of the genus Rhodococcus, and the expression of the nitrile hydratase in the transformant is confirmed.

(7) Deletion-plasmids and nitrile hydratase activity

Deletion-plasmids are prepared by deletion of various regions from the plasmid obtained in step (5). The resultant deletion-plasmids are used to identify which region is essential for the expression of nitrile hydratase. The region essential for the expression of nitrile hydratase, but not encoding nitrile hydratase, is thus identified.

(8) Nucleotide sequencing

The nucleotide sequence of the region identified in step (7) is determined.

*Rhodococcus rhodochrous* J-1 has been deposited as FERM BP-1478 with the National Institute of Bioscience and Human-Technology, Agency of Industrial Science and Technology, Japan. Transformant TG1/pNHJ10H (FERM BP-2777) containing plasmid pNHJ10H, transformant *Rhodococcus rhodochrous* ATCC12674/pK4 (FERM BP-3731) containing the hybrid plasmid vector pK4, and transformant JM109/pNHU10 (FERM BP-5224) containing plasmid pNHU10 have been deposited as substitutes for plasmid pNHJ10H, hybrid plasmid vector pK4, and plasmid pNHU10, respectively.

EFFECT OF THE INVENTION

The introduction of the regulatory gene of the invention along with the nitrile hydratase gene and its promoter region permits bacteria of the genus Rhodococcus to produce a higher level of nitrile hydratase. Other extraneous gene can also be introduced into a region downstream of the promoter to produce other proteins in high yield.

PREFERRED EMBODIMENTS OF THE INVENTION

Hereinafter, the present invention will be illustrated in detail by reference to the following Example, which however is not intended to limit the scope of the invention.

The following abbreviations are used in Example.
TE: 10 mM Tris-HCl (pH 7.8)-1 mM EDTA (pH 8.0)
TNE: 50 mM Tris-HCl (pH 8.0)-1 mM EDTA (pH 8.0)-50 mM NaCl
STE: 50 mM Tris-HCl (pH 8.0)-1 mM EDTA (pH 8.0)-35 mM sucrose
$2^x$YT medium: 1.6% trypton, 1% yeast extract, 0.5% NaCl
MY medium: 1% polypeptone, 0.3% yeast extract, 0.3% malt extract, 1% glucose (1) Preparation of total DNA

*Rhodococcus rhodochrous* J-1 (FERM BP-1478) was incubated at 28° C. for 2 days in 100 ml medium (glucose, $KH_2PO_4$, $K_2HPO_4$, $MgSO_4.7H_2O$, yeast extract, peptone, $CoCl_2$, urea, 1L water, pH 7.2). The bacterial cells were harvested by centrifugation and the pellet was washed with TNE and suspended in 10 ml TE. 4 ml of 0.25M EDTA, 10–20 mg lysozyme, 10–20 mg achromoprotease and 10 ml of 10% SDS were added to the suspension. The suspension was allowed to stand at 37° C. for 3 hours and then centrifuged. 0.7 ml of 2.5M sodium acetate and diethyl ether were added to 20 ml of the supernatant. The upper layer was discarded, and 2 volumes of ethanol was added to the lower layer. The DNA precipitates were recovered with a grass rod. The DNA was rinsed for 5 minutes each with TE:ethanol 2:1, 1:9 and 0:10 (v/v) and then dissolved in 2–4 ml TE. 10 µl of a mixture of RNase A and T1 was added to the solution and the mixture was incubated at 37° C. An equal amount of TE-saturated phenol was added to the mixture which was then centrifuged. More than equal amount of ether was added to the upper layer, and the lower layer was saved. The lower layer was dialyzed overnight against 2L TE containing a small amount of chloroform and further dialyzed for 3–4 hours against fresh TE buffer. 4 ml of crude total DNA was obtained.

(2) Construction of a DNA library

10 µl of plasmid pNHJ10H in which a 6.0 kb DNA fragment containing the H-type nitrile hydratase gene from J-1 had been inserted into vector pUC19 (Japanese Laid-Open Patent Publication No. 211379/1992; Biochim. Biophys. Acta 1129, 23–33 (1991)) was cleaved at 37° C. for 2 hours with a mixture of 2 µl each of restriction enzymes Sac I and Eco RI, 3 µl of reaction buffer ($10^x$) and 13 µl sterilized water, and the digest was electrophoresed on 1% agarose gel. The Sac I-Eco RI fragment, 0.37 kb long, was cut off from the gel and labeled with radioisotope $^{32}$P.

The total DNA from J-1 obtained in step (1) was digested with Eco RI and Eco RV, electrophoresed on an agarose gel and subjected to Southern hybridization where the 0.37 kb Sac I-Eco RI fragment prepared above was used as the probe. An about 4.3 kb DNA fragment containing a region upstream from the nitrile hydratase gene was hybridized with the probe. A fraction containing the 4.3 kb DNA fragment was eluted from the agarose gel.

Separately, 10 µl plasmid vector pUC19 was digested at 30° C. for 2 hours with a mixture of 2 µl each of restriction enzymes Sma I and Eco RI, 3 µl reaction buffer ($10^x$), and 13 µl sterilized water. The Sma I- and Eco RI-cleaved pUC19 was purified as follows: After an equal amount of TE-saturated phenol was added to the reaction solution, the solution was stirred and separated into upper (aqueous) and lower layers by centrifugation. The upper layer was extracted again with TE-saturated phenol in the same manner and further extracted twice with an equal amount of chloroform in the same manner. 3 µl of 3M sodium acetate and 90 µl ethanol were added to the upper layer, and the sample was allowed to stand at −80° C. for 30 minutes, centrifuged, dried and dissolved in TE.

A DNA library was prepared by inserting 3 µl of the above fraction containing the 4.3 kb fragment from the total DNA into the above Sma I- and Eco RI-cleaved pUC19 by the action of TAKARA ligation kit overnight at 4° C.

(3) Preparation of transformants and selection of a recombinant DNA

*E. coli* JM109 (available from Takara Shuzo Co., Ltd.) was inoculated into 10 ml of $2^x$YT medium and incubated at 37° C. for 12 hours. After incubation, the resultant culture inoculated into fresh $2^x$YT medium to a concentration of 1%, and the mixture was incubated for 2 hours. The culture was centrifuged and the pellet was suspended in 5 ml of cold 50 mM $CaCl_2$. The suspension was placed on ice for 40 minutes and then centrifuged again, the pellet was suspended in 0.25 ml of cold 50 mM $CaCl_2$. 60 µl of the recombinant plasmids (DNA library) prepared in step (2) was added to the suspension. The mixture was allowed to stand at 0° C. for 40 minutes and heat-shocked at 42° C. for 2 minutes, followed by addition of 1 ml of $2^x$YT medium. The mixture was incubated at 37° C. for 60 minutes with shaking. The culture, 100 µl per plate, was spreaded on a $2^x$YT agar plate containing 50 µg/ml ampicillin. The plate was incubated at 37° C. The colonies grown on the plate were selected for those carrying a DNA fragment upstream of the nitrile hydratase gene by colony hybridization in the following manner. The colonies grown on the plate were transferred to a nitrocellulose filter and the bacteria were lysed. The DNA was fixed on the filter and hybridized with the probe (0.37 kb fragment) obtained in step (2). The filter was autoradiographed and a colony containing the target recombinant DNA was selected. Additionally, the recombinant plasmid was extracted from the colony, and the Southern hybridization of the recombinant plasmid with the above probe indicated that the selected colony was a transformant carrying the target gene.

(4) Isolation and purification of the recombinant plasmid and construction of a restriction enzyme map The transformant selected in step (3) was incubated at 37° C. overnight in 100 ml of $2^x$YT medium, then collected and washed with TNE. 8 ml of STE and 10 mg lysozyme were added to the cells. The mixture was allowed to stand at 0° C. for 5 minutes. 4 ml of 0.25M EDTA, 2 ml of 10% SDS (at room temperature) and 5 ml of 5M NaCl were added to the mixture. The mixture was allowed to stand at 0° to 4° C. for 3 hours and ultracentrifuged. ½ volume of 30% PEG 6000 was added to the supernatant. The mixture was allowed to stand at 0° to 4° C. overnight and centrifuged again. TNE was added to the pellet to bring the volume up to 7.5 ml. CsCl was added to the suspension and centrifuged to remove proteins. Then, 300–500 mg/ml ethidium bromide was added to the supernatant and the mixture was transferred to a centrifuge tube. The tube was heat-sealed and ultracentrifuged. cccDNA was recovered. More than equal amount of isopropyl alcohol saturated with water was added to cccDNA to remove the ethidium bromide. The DNA sample was dialyzed against TE, resulting in about 3 ml of the purified recombinant plasmid. The recombinant plasmid thus obtained was designated pNHU10. This recombinant plasmid was digested with several restriction enzymes, and the restriction enzyme map thus prepared is shown in FIG. 1.

Figure 2:
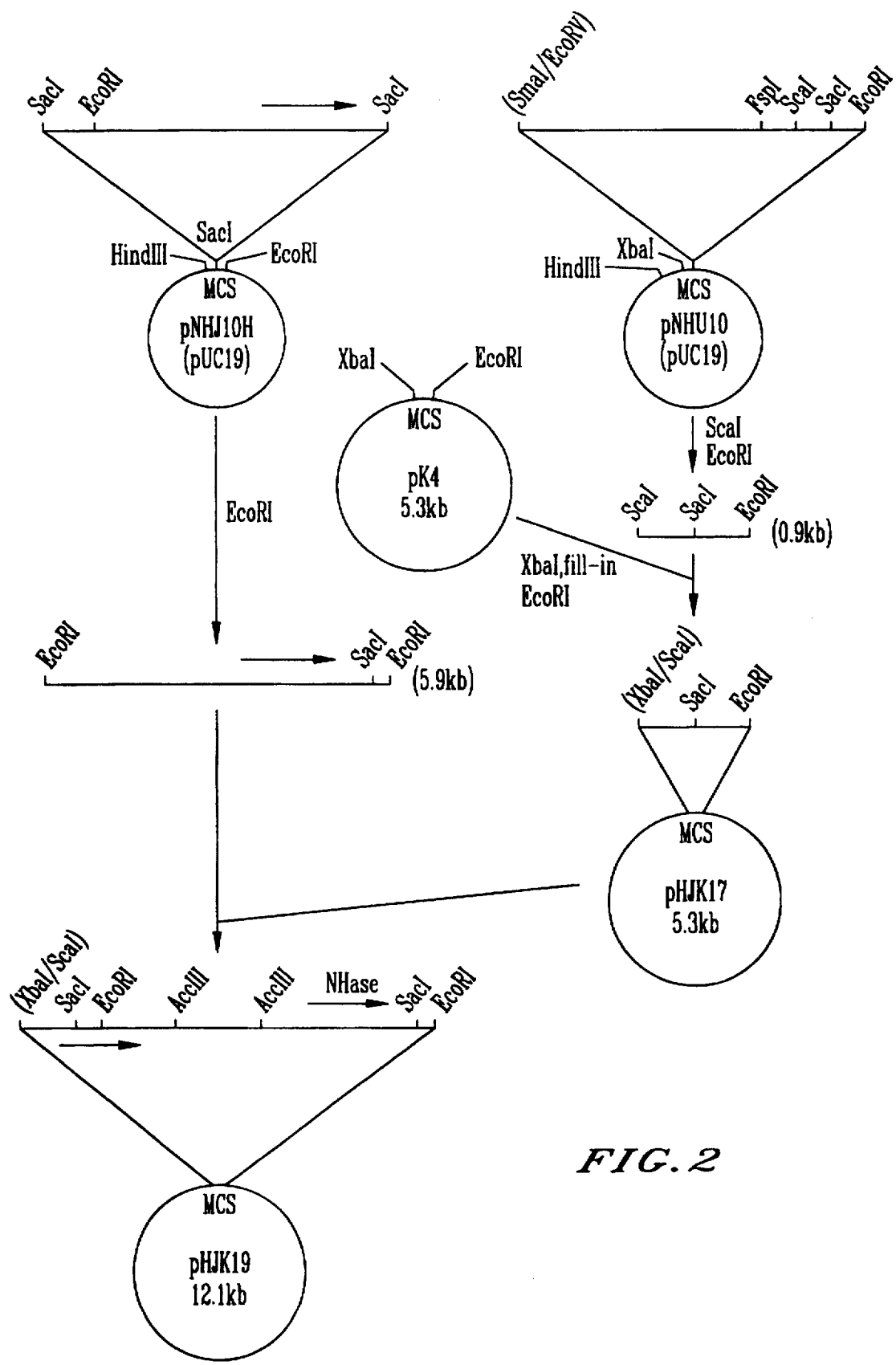
FIG. 2 shows the construction scheme of the recombinant plasmid pHJK19.

(5) Construction of a recombinant plasmid by inserting a fragment containing a regulatory gene and the nitrile hydratase gene into a plasmid vector capable of replicating in the genus Rhodococcus Plasmid pNHU10 obtained in step (4) overlapped with 0.37 kb nucleotides, and further contained 3.9 kb nucleotides upstream from, the nitrile hydratase gene derived from pNHJ10H. A 1.4 kb Fsp I-Eco RI fragment and a 0.9 kb Sca I-Eco RI fragment were excised from pNHU10 and inserted into the hybrid plasmid vector pK4 for *E. coli*—Rhodococcus bacteria to give plasmids pHJK16 and pHJK17, respectively. Plasmids pHJK18 and pHJK19 were constructed by inserting a 5.9 kb Eco RI fragment derived from pNHJ10H into plasmids pHJK16 and pHJK17, respectively. These steps are illustrated in FIGS. 1 and 2, respectively. In pHJK18 of FIG. 1, the thick arrow indicates the location and direction of the regulatory gene found in the present invention, and the thin arrow indicates the location and direction of the genes coding for 2 subunits of nitrile hydratase. In pHJK19 of FIG. 2, the thick arrow indicates the location and direction of the regulatory gene found in the present invention, and the thin arrow indicates the location and direction of the genes coding for 2 subunits of nitrile hydratase.

(6) Transformation of bacteria of the genus Rhodococcus and production of nitrile hydratase by the transformant

*Rhodococcus rhodochrous* ATCC12674 at the logarithmic growth phase was harvested by centrifugation, washed 3 times with ice-cold sterilized water and suspended in 15% PEG 6000 (polyethylene glycol 6000) to a final concentration of at least $10^9$ cells/ml. 1 µg of plasmid pHK18 DNA or pHK19 DNA was mixed with 100 µl of the bacterial suspension and the mixture was cooled on ice. This mixture of DNA and bacteria was introduced into a gene pulser chamber, cooled on ice and pulsed with a electrostatic capacity of 25 µF, resistance of 400Ω and voltage of 20 kV/cm.

The bacterial suspension thus treated was placed on ice for 10 minutes and heated at 37° C. for 5 minutes. 1 ml of MY medium was added to the suspension, which was then shaken at 28° C. for 3 hours. The bacterial suspension was spreaded on an MY agar plate containing 50 µg/ml kanamycin and incubated at 25° C. for 2 days. The colony grown on the plate was streaked on another MY agar plate containing kanamycin, and their resistance to kanamycin was ascertained by their growth on the plate.

The resultant *Rhodococcus rhodochrous* transformants (*Rhodococcus rhodochrous* ATCC12674/pHJK18 and *Rhodococcus rhodochrous* ATCC12674/pHJK19) were incubated at 28° C. for 2 days in a medium (10 g glycerol, 5 g peptone, 3 g yeast extract, 3 g malt extract, 1 g $KH_2PO_4$, 1 g $K_2HPO_4$, 0.01 g $CoCl_2.6H_2O$, 0.75 g or 3.75 g urea (pH 7.0)/1L medium). The bacterial cells were harvested by centrifugation, and the pellet was washed with 150 mM NaCl and suspended in 0.1M HEPES-KOH buffer (pH 7.2) containing 0.35% n-butyric acid. The cells were disrupted by sonication and centrifuged to remove the cell membrane. The cell extract thus obtained was examined for nitrile hydratase activity. The enzyme assay was carried out in a reaction mixture containing 0.5 ml of 100 mM potassium phosphate buffer (pH 7.0), 1 ml of 200 mM acrylonitrile and 0.5 ml of the cell extract diluted with a suitable amount of water. The reaction was carried out at 20° C. for 10 minutes and stopped by the addition of 0.2 ml of 1N HCl. The amount of acrylamide formed in the reaction mixture was determined by HPLC.

Table 1 shows the nitrile hydratase activities of the cell-free extracts from *Rhodococcus rhodochrous* ATCC12674/pHJK18 and *Rhodococcus rhodochrous* ATCC12674/pHJK19. In the table, urea is an inducer for nitrile hydratase.

TABLE 1

| | nitrile hydratase activity urea (g/L) | | |
|---|---|---|---|
| transformant | 0 | 0.75 | 3.75 |
| *Rhodococcus rhodochrous* ATCC12674/pHJK18 | 171 | 279 | 115 |
| *Rhodococcus rhodochrous* ATCC12674/pHJK19 | 180 | 242 | 104 |

(unit/mg protein)

(7) Deletion plasmids and nitrile hydratase activity

Because it was estimated that region not involved in the expression of nitrile hydratase still remained in pHJK18 and pHJK19, deletion plasmids were prepared therefrom and examined for nitrile hydratase activity. The result indicated that the regulatory gene involved in the expression of the activity was located within an about 1.9 kb region between the Sca I and Acc III sites.

(8) Nucleotide sequencing

The nucleotide sequence of the region identified in step (7) was sequenced by the chain termination method (Sanger F. Science, 214, 1205–1210 (1980)) using DNA polymerase. The sequence analysis revealed the presence of a long open reading frame coding for the amino acid sequence shown in the Sequence Listing by SEQ ID: No. 1. The nucleotide sequence of the open reading frame is shown in the Sequence Listing by SEQ ID: No. 2.

What is claimed is:

1. An isolated regulatory gene coding for a polypeptide having the ability to activate a promoter for a nitrile hydratase gene and having the amino acid sequence defined in the Sequence Listing by SEQ ID No: 1.

2. The gene according to claim 1 wherein the regulatory gene coding for a polypeptide having the ability to activate a promoter for a nitrile hydratase gene possesses the nucleotide sequence defined in the Sequence Listing by SEQ ID No: 2.

3. A recombinant DNA wherein the regulatory gene of claim 1 or 2 and a nitrile hydratase gene containing a promoter region have been inserted into a vector.

4. A transformed host cell containing the recombinant DNA of claim 3.

\* \* \* \* \*

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 361 base pairs (B) TYPE: amino acid
(C) TOPOLOGY: linear (ii) MOLECULE TYPE: protein (iii) ORIGINAL SOURCE:
(A) ORGANISM: Rhodococcus rhodochrous
(B) STRAIN: J-1

(xi) SEQUENCE DESCRIPTION: SEQ ID NO:1:

```
Met Pro Leu Arg Arg Leu Asn Leu Gly Leu Val Leu Pro Gln Ser Gly
                  5                  10                  15
Pro Ser Gly Ile Phe Gly Pro Ser Cys Gln Ala Ser Ala Glu Tyr Ala
             20                  25                  30
Ile Asp Glu Leu Asn Ala Gly Gly Gly Ile Leu Gly Arg Glu Val Thr
         35                  40                  45
Ala Val Phe Val Asp Gly Gly Ala Asp Pro Ser Ala Val Ala Ala Cys
     50                  55                  60
Ile Ala Asp Gln Thr Lys Arg Arg Glu Leu Asp Ala Val Val Gly Trp
 65                  70                  75                  80
His Thr Ser Ala Val Arg Arg Arg Ile Val Ser Ala Ile Gly Gly Arg
                 85                  90                  95
Ile Pro Tyr Val Tyr Thr Ala Val Tyr Glu Gly Gly Glu Asn Ser Asp
                100                 105                 110
Gly Val Phe Met Thr Gly Glu Val Pro Thr Asn Gln Ile Leu Pro Ala
            115                 120                 125
Leu Glu Trp Met Thr Glu Ile Gly Val Arg Lys Trp Tyr Val Ile Gly
    130                 135                 140
Ser Asp Tyr Val Trp Pro Arg Lys Thr Val Ser Val Ile Arg Glu Phe
145                 150                 155                 160
Leu Ala Ser Asn Gln Leu Pro Ser Arg Gly Arg Ser Asp Val Arg Leu
                165                 170                 175
Ala Ser Cys Glu Phe Leu Ser Leu Gly Thr Ser Asp Phe Thr Ser Thr
            180                 185                 190
Leu Glu Ala Ile Glu Met Ser Gly Ala Asp Gly Val Leu Val Leu Leu
        195                 200                 205
Leu Gly Gln Asp Ala Val Gln Phe Asn Arg Ser Phe Ser Arg Lys Gly
    210                 215                 220
Leu His Arg Asp Ile Val Arg Leu Ser Pro Leu Met Asp Glu Asn Met
225                 230                 235                 240
Leu Leu Ala Ser Gly Ala His Ala Ala His Gly Leu Tyr Ser Val Ser
                245                 250                 255
Gly Phe Phe Glu Cys Leu Val Thr Gly His Ser Met Asp Phe Glu Ser
            260                 265                 270
Arg Tyr Ile Lys His Phe Gly Pro Thr Ala Pro Pro Ile Thr Ser Pro
        275                 280                 285
Gly Glu Ser Cys Tyr Glu Gly Ile Arg Leu Leu Ala Thr Leu Ala Asp
    290                 295                 300
Arg Ala Gly Asp Leu Asp Pro Met Ser Leu Ser Tyr His Ala Asp Arg
305                 310                 315                 320
Thr Leu Asp Tyr Asp Ser Pro Arg Gly His Val Arg Phe Asp Gly Arg
                325                 330                 335
His Leu Ala Gln Asp Met Tyr Ile Ala Arg Ala Asp Gly Val Glu Phe
            340                 345                 350
Asp Val Leu Ala Gln Val Ser His Val
        355                 360
```

-continued (2) INFORMATION FOR SEQ ID NO:2:

(i) SEQUENCE CHARACTERISTICS:
        (A) LENGTH: 1086 base pairs
        (B) TYPE: nucleic acid
        (C) STRANDEDNESS: double
        (D) TOPOLOGY: linear (ii) MOLECULE TYPE: protein (iii) ORIGINAL SOURCE:
        (A) ORGANISM: Rhodococcus rhodochrous
        (B) STRAIN: J-1

(xi) SEQUENCE DESCRIPTION: SEQ ID NO:2:

```
GTG CCC CTC CGC CGA CTG AAC CTG GGC TTG GTG CTA CCT CAG AGT      45
GGA CCG TCC GGC ATT TTC GGT CCG TCA TGC CAG GCG AGC GCC GAG      90
TAC GCC ATC GAT GAG CTC AAC GCG GGC GGC GGA ATC CTG GGC CGA     135
GAG GTT ACG GCG GTC TTC GTT GAC GGG GGC GCG GAC CCG TCC GCC     180
GTA GCA GCA TGC ATC GCC GAC CAG ACG AAA CGT CGG GAA TTG GAC     225
GCC GTA GTC GGG TGG CAC ACG TCT GCT GTT CGT CGA CGC ATC GTG     270
AGC GCC ATC GGC GGA CGT ATT CCG TAT GTC TAC ACC GCA GTC TAC     315
GAG GGC GGC GAG AAC TCC GAC GGC GTG TTC ATG ACG GGA GAG GTA     360
CCG ACG AAT CAG ATT CTT CCT GCC CTG GAA TGG ATG ACT GAG ATC     405
GGC GTG CGT AAG TGG TAT GTC ATT GGC AGT GAC TAC GTT TGG CCT     450
CGA AAG ACT GTC TCG GTC ATT CGC GAA TTC CTG GCG TCG AAC CAG     495
CTA CCG AGT CGA GGC CGC AGC GAC GTT CGA CTG GCG TCG TGC GAG     540
TTC TTG TCA CTA GGC ACA TCC GAC TTC ACT TCA ACG CTC GAA GCA     585
ATT GAG ATG TCG GGG GCC GAT GGC GTT CTC GTC CTC CTC CTC GGC     630
CAG GAC GCA GTA CAG TTC AAC CGG TCT TTT TCA CGG AAA GGG CTG     675
CAC CGC GAC ATC GTC AGA CTC AGT CCG CTG ATG GAC GAG AAC ATG     720
CTG TTG GCA AGC GGC GCA CAC GCC GCG CAC GGA CTC TAC TCG GTG     765
TCG GGG TTC TTC GAG TGC CTG GTC ACC GGG CAC AGC ATG GAT TTC     810
GAA TCC AGG TAC ATC AAG CAC TTC GGT CCG ACC GCC CCG CCG ATC     855
ACT TCG CCT GGA GAG TCG TGC TAC GAG GGC ATT CGG CTG TTG GCC     900
ACT CTT GCA GAC CGG GCC GGC GAT CTC GAC CCG ATG TCT CTG AGC     945
TAT CAC GCA GAC CGT ACC CTC GAC TAC GAC AGC CCT CGA GGC CAT     990
GTC CGC TTC GAT GGT CGC CAT CTC GCT CAG GAC ATG TAC ATC GCG    1035
CGG GCT GAC GGA GTA GAG TTC GAC GTC TTA GCG CAG GTT TCC CAT    1080
GTG TGA                                                         1086
```